United States Patent [19]

Takematsu et al.

[11] 4,129,435

[45] Dec. 12, 1978

[54] AGRICULTURAL CHEMICAL/RESIN COMPOSITIONS

[75] Inventors: Tetsuo Takematsu, Utsunomiya; Fusayoshi Masuda, Kyoto; Kenji Tanaka, Ootsu; Kazuo Nishida; Akira Nakamura, both of Kyoto, all of Japan

[73] Assignee: Sanyo Chemical Industries, Ltd., Kyoto, Japan

[21] Appl. No.: 708,714

[22] Filed: Jul. 26, 1976

[51] Int. Cl.$^2$ .................. A01N 7/00; A01N 17/08
[52] U.S. Cl. ............................................ 71/65; 71/79; 71/92; 71/93; 71/94; 71/105; 71/100; 71/111; 71/113; 71/114; 71/116; 71/117; 71/118; 71/120; 71/121; 71/122; 71/DIG. 1; 424/219; 526/3; 526/5; 526/6; 528/76
[58] Field of Search .................. 71/DIG. 1, 79, 65

[56] References Cited

U.S. PATENT DOCUMENTS

| | | | |
|---|---|---|---|
| 3,539,373 | 11/1970 | Cooke | 117/3 |
| 3,838,075 | 9/1974 | Dietrich et al. | 71/DIG. 1 |
| 3,891,423 | 6/1975 | Stanley et al. | 71/DIG. 1 |
| 3,920,436 | 11/1975 | Janssen | 71/DIG. 1 |
| 3,979,198 | 9/1976 | Bardsley | 71/DIG. 1 |

FOREIGN PATENT DOCUMENTS 4635400 10/1971 Japan .................. 71/DIG. 1

*Primary Examiner*—Glennon H. Hollrah
*Attorney, Agent, or Firm*—Oblon, Fisher, Spivak, McClelland & Maier

[57] ABSTRACT

An agricultural chemical composition which has improved efficiency, long range effectiveness and decreased phytotoxicity to useful plants is prepared by mixing an agricultural chemical with a filmforming polymer having a soil fixity of at least 40% and a water vapor permeability of 400 – 1,500 g/m$^2$/24 hrs.

5 Claims, 1 Drawing Figure

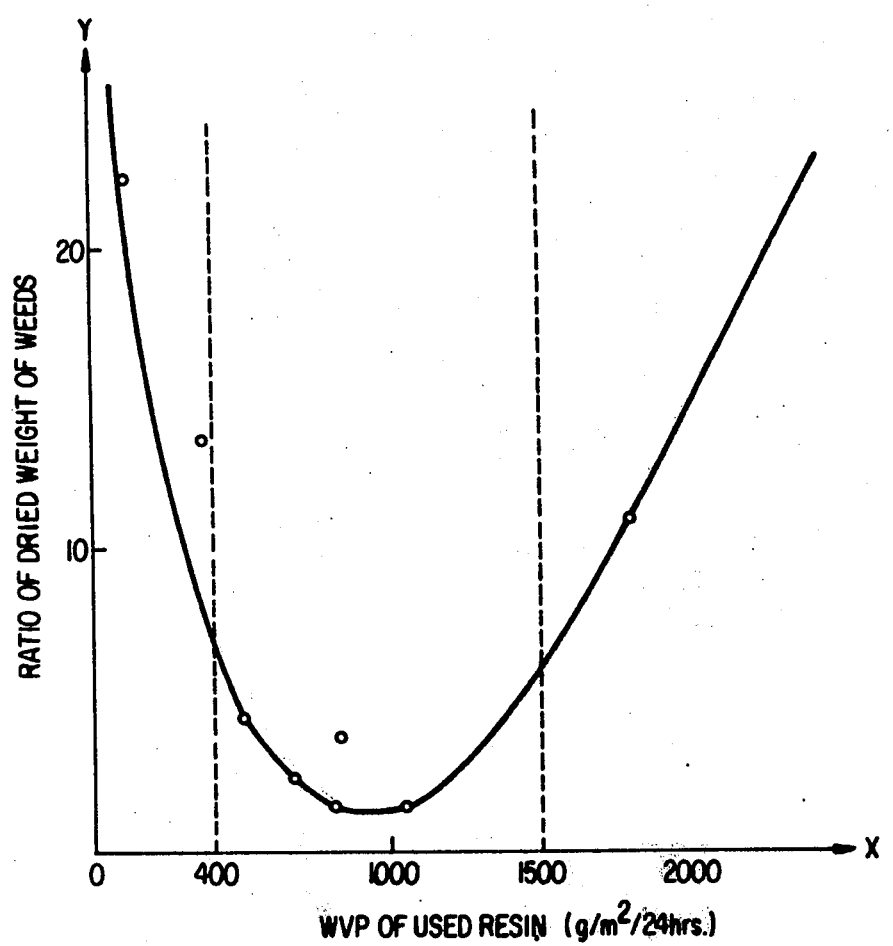

AGRICULTURAL CHEMICAL/RESIN COMPOSITIONS

BACKGROUND OF THE INVENTION

1. Field Of The Invention

This invention relates to agricultural chemical (agrochemical) compositions containing specific film-forming resins. More specifically, it relates to agrochemical compositions which have the improved efficiency, long range effectiveness and decreased phytotoxicity to useful plants, and methods of imparting the above properties to agrochemicals.

2. Description Of Prior Art

Recently, various agrochemicals have come into wide use to simplify various aspects of farm work, e.g., labor saving materials, and the use of these chemicals has contributed much to increased crop yields. However, the conventional methods of using agrochemicals have the disadvantage that the agrochemicals must be applied to plants or to soils in large amounts and high frequency in order to obtain good results, because, in a rather short time, the chemical agents may be washed by rain into the subsoil, degraded by bacteria in the soil, or escape in vapor, resulting in reduced effectiveness of the agrochemicals. In addition, some herbicides tend to be so easily eluted with water from the upper soil into the subsoil that they are rendered ineffective and that, sometimes, they adversely affect germination or growth of useful plants, or cause withering of useful plants which usually have their roots in the subsoil.

On the other hand, the hazard due to excessive use of agrochemicals has been a major problem of society in view of increased understanding of environmental problems. Therefore, the improvement of the above-mentioned drawbacks has been expected.

To improve these disadvantages, heretofore, spreaders (e.g., nonionic and anionic surfactants) have been incorporated in agrochemical compositions, but they are unsatisfactory for preventing agrochemicals from leaching by water and escaping in vapor. Other methods have been proposed to overcome the above disadvantages in which methods agrochemicals are coated with a resin, or they are formulated with a resin, or, at the time of their application, they are mixed with a resin. Some examples of the resin are polyvinyl chloride, polyethylene, polystyrene, polyacrylates, polyvinyl acetate and epoxy resins. These methods are insufficient to overcome the above disadvantages, and, furthermore, some are effective only for some limited agrochemicals, and others are difficult to apply, e.g., too high a viscosity, or too short in handling time to apply by a conventional sprayer.

SUMMARY OF THE INVENTION

Accordingly, it is an object of this invention to provide an agrochemical composition which possesses improved efficiency, continuous effectiveness and decreased phytotoxicity to useful plants.

It is another object of this invention to provide an agrochemical composition which comprises a specific film-forming polymer (1) which prevents an agrochemical from being leached by water into the subsoil, and from escaping as a vapor, and (2) which moderately controls elution of an agrochemical.

It is a still another object of this invention to provide a method of imparting the above-mentioned properties to an agrochemical.

These and other objects of this invention, as will hereinafter become more readily apparent, can be attained by a composition which comprises at least one agrochemical and a film-forming polymer having a soil fixity of at least 40% and a water vapor permeability of 400–1,500 g/m$^2$/24hrs.

BRIEF DESCRIPTION OF THE DRAWING

In describing this invention, reference shall be made to the accompanying Drawing in which FIG. 1 is depicting by a graph the relation of dried weight ratio of weeds to water vapor permeability.

DETAILED DESCRIPTION OF THE INVENTION

In this invention, the soil fixity of a resin will be determined by the following method: 20 ml of 1 weight % aqueous solution or water suspension of a resin to be tested is allowed to permeate through a glass column (15 cm long, 2 cm in diameter) filled densely with 15g of fine sand (particle size of 100–300 mesh, moisture content of 6 weight %). The filtered solution, (which is obtained from the bottom of the column) is dried, and residue is weighed. If the weight of residue is a gram, the soil fixity (X%) can be calculated from the following equation:

$$X(\%) = 100 \times (0.2 - a)/0.2$$

In this invention, the water vapor permeability (WVP) will be determined by the method of JIS-Z-0208 (Japanese Industrial Standard). That is, a cup (15 mm deep, 60 mm in diameter) containing 10 g of dried CaCl$_2$ (particle size of 8–30 mesh) is covered closely with the film 0.03 mm thick of a resin to be tested. The cup is allowed to stand for 24 hrs. in the box maintained at 40°±1° C. and relative humidity of 90±2%, and weighed. The water vapor permeability (Y) is calculated from the following equation:

$$Y (g/m^2/24hrs) = \frac{[\text{Cup weight (g) after 24 hrs.}] - [\text{Initial cup weight (g)}]}{[\text{Permeable area of the cup (m}^2\text{)}]}$$

Suitable agrochemicals used in the invention include herbicides, insecticides, fungicides, nematocides, rodenticides, plant growth regulators, repellents and attractants. Among these, the preferred are herbicides, insecticides and fungicides, and the more preferred are agrochemicals which are easily leached by water into the subsoil and/or are voltailized into in the atmosphere. Examples of the herbicides used in the invention are:

A. Urea-type herbicide (A-1) 3-(3,4-dichlorophenyl)-1,1-dimethylurea [DCMU]
(A-2) 3-(4-chlorophenyl)-1,1-dimethylurea [CMU]
(A-3) 3-[4-(4-chlorophenoxy)phenyl]-1,1-dimethylurea [Tenoran]
(A-4) 3-(3,4-dichlorophenyl)-1-methoxy-1-methylurea [Linuron]
(A-5) 1-(2-methylcyclohexyl)-3-phenylurea [Siduron]
(A-6) 3-cyclooctyl-1,1-dimethyl urea [Cycluron]

B. Triazine-type herbicide (B-1) 2-chloro-4-ethylamino-6-isopropylamino-S-triazine [Atrazine]

(B-2) 2-chloro-4,6-bis(ethylamino)-S-triazine [Simazine]

(B-3) 2-methylthio-4,6-bis(isopropylamino)-S-triazine [Prometryne]

C. Uracil-type herbicide (C-1) 5-bromo-3-sec-butyl-6-methyl uracil [Bromacil]

(C-2) 3-cyclohexyl-5,6-trimethylene uracil [Lenacil]

D. Chloro-acetamide-type herbicide (D-1) 2-chloro-2′,6′-diethyl-N-(methoxymethyl) acetanilide [Alachlor]

(D-2) 2-chloro-N-isopropyl acetanilide [Propachlor]

(D-3) N,N-diethyl-2-chloro acetamide [CDEA]

(D-4) N,N-diallyl-2-chloroacetamide [CDAA]

E. Amide-type herbicide (E-1) N,N-dimethyl-2,2-diphenyl acetamide [Diphenamid]

F. Aliphatic acid-type herbicide (F-1) 2,2-dichloropropionic acid (Na salt) [DPA]

(F-2) trichloroacetic acid (Na salt) [TCA]

(F-3) 2,2,3,3-tetrafluoro propionic acid (Na salt) [TFP]

G. Picolinic acid-type herbicide (G-1) 4-amino-3,5,6-trichloropicolinic acid [Picloram]

H. Phenoxy-type herbicide (H-1) 2,4-dichlorophenoxy acetic acid [2,4-D]

(H-2) 2-methyl-4-chlorophenoxy acetic acid [MCP]

(H-3) 2-(2′-methyl-4′-chlorophenoxy) propionic acid [MCPP]

(H-4) α-(2-methyl-4-chlorophenoxy)-butylic acid [MCPB]

I. Carbamate-type herbicide (I-1) isopropyl-N-(3-chlorophenyl) carbamate [CIPC]

(I-2) methyl-N-(3,4-dichlorophenyl) carbamate [SWEP]

(I-3) 2-chloroethyl-N-(3-chlorophenyl) carbamate [BIPC]

J. Thiol carbamate-type herbicide (J-1) S-ethyl-N,N-di-n-propyl thiolcarbamate [EPTC]

(J-2) S-n-propyl-N,N-di-n-propyl thiolcarbamate [Vernolate]

(J-3) S-n-propyl-N-ethyl-N-butyl-thiolcarbamate [Pebulate]

K. Nitrile-type herbicide (K-1) 2,6-dichlorobenzonitrile [DBN]

(K-2) 2,6-dichlorothiobenzamide [DCBN]

L. Toluidine-type herbicide (L-1) α,α,α-trifluoro-2,6-dinitro-N,N-dipropyl-P-toluidine [Trifluralin]

(L-2) N-butyl-N-ethyl-α,α,α-trifluoro-2,6-dinitro-P-toluidine [Benefin]

(L-3) N,N-dipropyl-2,6-dinitro-4-methylsulfonyl aniline [Nitralin]

M. Phenol-type herbicide (M-1) 4,6-dinitro-O-sec-butyl phenol (alkanol amine salt) [DNBP]

N. Others (N-1) 3-amino-1,2,4-triazole [ATA]

(N-2) 3,(2-methylphenoxy)-pyridazine [Credazine]

(N-3) N-1-naphtyl phthalamic acid (Na salt) [NPA]

Among the above herbicides, the preferred are urea-, triazine-, uracil-, chloroacetamide and amide-types upon consideration of prevention from being leached by water, and are carbamate-, thiolcarbamate-, nitrile-, toluidine- and phenol-types upon consideration of prevention from escaping as a vapor.

The film-forming resin used in the invention is a hydrophilic resin having a soil fixity of at least 40% (preferably at least 50%) and a water vapor permeability of 400–1,500 g/m$^2$/24hrs (preferably 600–1,000), and the objects of the invention are not attained by hydrophobic or water-soluble resins which do not have the above values. The hydrophobic resin has fairly good preventing effects of being leached and of escaping in vapor, but it is very poor at controlling elution of an agrochemical. On the other hand, the water-soluble resin is insufficient in any of the above effects.

The film-forming, hydrophilic resin used in the invention, generally, belongs to the resins which have one or more hydrophilic groups such as polyoxyethylene chain, carboxyl (including anhydrides thereof), carboxylic acid salt, amide, sulfonic acid, sulfonic acid salt, hydroxyl, quaternary ammonium salt groups. Typical examples of the resin used in the invention are as follows:

(1) Polyurethanes, which are produced by the reaction of organic polyisocyanates and polyol components and having a polyoxyethylene moiety (and optionally chain extenders). Examples of the polyols are conventional polyetherpolyols [obtained by adding ethylene oxide (optionally with other alkylene oxides such as propylene oxide, butylene oxides) to a compound having at least two active hydrogen atoms]. Molecular weight of the polyols may be, for example, 500–20,000;

(2) Polyester resins, which are produced by the condensation reaction of organic polycarboxylic acids or their alkyl esters and polyol components having polyoxyethylene moiety;

(3) Vinyl co-polymers, which are produced by the reaction of one or more water-soluble unsaturated monomers and other water-insoluble monomers. The water-soluble unsaturated monomers are, for example, carboxylic group-containing unsaturated monomers (e.g., acrylic acid, methacrylic acid, crotonic acid, maleic acid, fumaric acid and maleic anhydride, etc.), sulfonic group-containing unsaturated monomer (e.g., sulfopropyl(meth)acrylates, etc.), amide group-containing unsaturated monomer (e.g., acrylamide, N-methylol acrylamide, etc.), hydroxyl group-containing unsaturated monomer (e.g., hydroxyethyl(meth)acrylates, etc.), and quaternary ammonium salt group-containing unsaturated monomer (e.g., N,N,N-trimethyl-N-acryloyloxyethyl ammonium halides, etc.). The salts of these monomers are also used (alkali metal salts, ammonium salts, amine salts, etc.), if they are able to form salts. The water-insoluble unsaturated comonomers are, for example, alkyl(meth)acrylates (e.g., methylmethacrylate, butylacrylate), acrylonitrile, styrene, vinyl acetate, vinylidene chloride, butadiene, alkenes (e.g., ethylene, prolylene, butylene).

Among these hydrophilic resins, the desired ones are polyurethanes and polyester resins which contain the polyoxyethylene moiety (molecular weight of 300–10,000) as the hydrophilic group, because of the case of control of soil fixity and WVP, excellent effects and low costs. The particularly desirable are the emulsion of the above polyurethanes and polyester resins, because of the case encounted in producing an agrochemical-resin composition, and the ease of applying the composition to the farm. The preparation of these emulsions is carried out by conventional methods. For example, they are the method of emulsifying aforesaid resin in water with the aid of emulsifying or dispersing agents, and the method of emulsifying a polyurethane pre-polymer (which is prepared by the reaction of 1 mole of a polyol and more than 1 mole of a polyisocyanate) in water with the aid of emulsifying or dispersing agents.

The methods of preparing the agrochemical-resin compositions of this invention are not particularly limited. When the resins are used with a spray-type agrochemical (e.g., wettable powder, emulsion and solution formulation), for example, the use of resin emulsion is preferable from the point of the ease of application, because a conventional sprayer can be used. The method of mixing may be selected from the following:

(1) fixed quantity of an agrochemical and a concentrated resin emulsion are mixed with the diluting water, (2) a concentrated resin emulsion is mixed with the diluting water which contains an agrochemical, (3) an agrochemical is premixed with resin emulsion and then diluted with water.

In another method of preparing the agrochemical-resin composition of this invention, a concentrated emulsion-type composition is prepared by mixing an agrochemical with the resin emulsion of this invention during or after the production of the resin emulsion, or by emulsifying a mixture of agrochemical and resin. The resulting concentrated composition is applied by a conventional manner.

The granular, pellet, dust type of composition of this invention may be prepared by mixing and formulating the agrochemical and the resin of this invention and, if necessary, carrier (e.g., bentonite, clay, diatomaceous earth, talc, aluminum oxide, fine sand and the like). Thus, the composition is prepared (1) by coating or mixing, and agrochemical with the emulsion or organic solvent solution of the resin, followed by changing into granular or dust, or (2) by preparing the resin film containing agrochemicals, followed by cutting or pulverizing.

In the present invention, the ratio of agrochemicals and resins may vary widely depending upon the method of final application and the type of agrochemicals. In general, they may be employed in the weight ratio of 1 part of agrochemical (active ingredient) to 0.1 to 200 parts (preferably 0.2–100 parts) of resins (solid content).

Other materials, such as surfactants, emulsion stabilizers, pigments, lubricants, fillers, plasticizers, antiseptic substances, ultraviolet stabilizers, dyes, and the like, may be included in the compositions of the invention.

The present invention has the following advantages:

(1) The phytotoxicity to useful plants is reduced because the agrochemical is prevented from being leached by water into the subsoil, (2) Agrochemicals, which have been used only in autumn and winter seasons because of their volatility, can be used in all seasons because their volatilization and escape into the atmosphere can be prevented.

(3) The dosage applied can be decreased because the efficiency of the agrochemical is improved, and therefore is is very economical and improves environmental conditions.

(4) The frequency of application of the agrochemical can be reduced because of improved long term effectiveness, and therefore results in labor savings.

(5) The duration of the period of effectiveness of the agrochemical can be controlled by adjusting the WVP or amount of resin used.

(6) A conventional applicator or sprayer for agricultural use is applicable for the compositions of the present invention.

The following examples will illustrate the nature and advantages of the present invention. It should be understood, however, that the examples are merely illustrative and are not to be regarded as limitations to the appended claims. Unles otherwise indicated, the parts are by weight.

EXAMPLE 1

13 parts of poly(oxyethylene oxypropylene)glycol [average molecular weight (MW) is 4,000, molar ratio of oxyethylene and oxypropylene is 80:20], 65 parts of polypropylene glycol (MW 950) and 22 parts of tolyene-di-isocyanate (TDI) were charged into the reaction vessel equipped with an agitator, a nitrogen bubbling tube and a thermometer. The above mixture was reacted at 75°–85° C. for 8 hrs. under nitrogen atmosphere to obtain the urethane prepolymer having 4.6% of free isocyanate radicals. To 100 parts of this urethane prepolymer there was added 5 parts of polyoxyethylene nonylphenyl ether (nonionic emulsifier) and 10 parts of alkyl ethersulfate (anionic emulsifier) at 20° C. The resultant mixture was emulsified in 170 parts of water with continuous agitating to obtain urethane emulsion [A]. The film from the emulsion had WVP of 807 $g/m^2/24hrs$ and a soil fixity of 78%.

5Kg of the emulsion [A] and each of the herbicides, whose kind and amount active ingredient are listed in Table 1, were mixed with 300 l of water to obtain the spraying samples.

In the 1/100 $m^2$ pots charged with loam soil, radish and wheat were seeded respectively and covered with loam soil 3 cm deep which was mixed with weed seeds of *Digitaria adscendens* and *Amaranthus retroflexus*. Over the resultant pots, the above liquid samples were sprayed uniformly in amounts of 300 $ml/m^2$.

After 20 days, the herbicidal effects and the degree of phytotoxicity to radish and wheat were observed. The resulting data are presented in Table 1. For comparative purposes data are also presented in the table showing the results obtained for radish and wheat samples which were not treated with a herbicide and for radish and wheat samples which were treated with the urethane emulsion free of herbicide.

Table 1

| Herbicide | Amount of Herbicide (Kg) | Emulsion [A] | Herbicidal effect Digitaria adscendens | Amaranthus retroflexus | Phytotoxicity Wheat | Radish |
|---|---|---|---|---|---|---|
| D C M U | 0.05 | added | 5 | 5 | 0 | 0 |
| D C M U | 0.05 | — | 4 | 4 | 1 | 2 |
| Atrazine | 0.05 | added | 5 | 5 | 0 | 0 |
| Atrazine | 0.05 | — | 4 | 4 | 2 | 3 |
| Bromacil | 0.05 | added | 5 | 5 | 0 | 0 |
| Bromacil | 0.05 | — | 5 | 5 | 2 | 5 |
| Alachlor | 0.05 | added | 5 | 5 | 0 | 0 |
| Alachlor | 0.05 | — | 5 | 5 | 3 | 0 |
| Diphenamid | 0.1 | added | 4.5 | 4 | 0 | 0 |
| Diphenamid | 0.01 | — | 3 | 3 | 2 | 0 |
| D P A | 0.3 | added | 4 | 0 | 0 | 0 |
| D P A | 0.3 | — | 2.5 | 0 | 2.5 | 0 |
| Picloram | 0.05 | added | 4.5 | 5 | 0 | 0 |
| Picloram | 0.5 | — | 2 | 5 | 0 | 2 |
| D B N | 0.1 | added | 4 | 5 | 0 | 0 |
| D B N | 0.1 | — | 1.5 | 4 | 2 | 0 |
| C-IPC | 0.1 | added | 5 | 5 | 0 | 0 |
| C-IPC | 0.1 | — | 3 | 2 | 0 | 0 |
| E P T C | 0.2 | added | 5 | 5 | 1 | 0 |
| E P T C | 0.2 | — | 4 | 2.5 | 5 | 0 |
| Trifluralin | 0.05 | added | 5 | 5 | 0 | 0 |
| Trifluralin | 0.05 | — | 3.5 | 4 | 2.5 | 0 |
| Untreatment | | | 0 | 0 | 0 | 0 |
| Urethane | emulsion [A] only | | 0 | 0 | 0 | 0 |

Note:
The evaluation was indicated by the number from 0 to 5. 0 means non-effective in the same as in untreated, and 5 means quite excellent result.

Table 1 shows that the composition of this invention gives excellent results from the viewpoint of herbicidal effects and the prevention of phytotoxicity to useful plants in comparison with the use of the commercial herbicides only.

These excellent results come from preventing herbicides from being leached by water into subsoil or from escaping in vapor as indicated in Table 2 and 3. The data in Table 2 were obtained by the following method: The above liquid samples were sprayed in amount of 300 ml/m² in the pots, which were made by piling up 10 rings (1 cm high, 10 cm in diameter), and filled with loam soil. After 24 hrs, 20 mm/hr of artificial rainfall was allowed to fall for 1 hr., and then the soil was separated into 10 pieces by the rings. In these soils, the radish or sawa millet was seeded, and after 20 days the degree of phytotoxicity was observed.

The data in Table 3 were measured by the following method: The above liquid samples were sprayed uniformly in amounts of 300 ml/m² on the soils which contained the speeds of Digitaria adscendens and Amaranthus retroflexus. For the first 4 days, these soils were maintained under dry condition without sprinkling water, and then sprinkled everyday. After 20 days, the herbicidal effects were observed.

Table 2

| Depth of the soil | Phytotoxicity to radish Atrazine only | Atrazine and [A] | Phytotoxicity to radish Picloram only | Picloram and [A] | Phytotoxicity to sawa millet Bromacil only | Bromacil and [A] |
|---|---|---|---|---|---|---|
| 0 – 1 cm | 70 (%) | 100 (%) | 50 (%) | 100 (%) | 100 (%) | 100 (%) |
| 1 – 2 | 80 | 100 | 70 | 100 | 100 | 100 |
| 2 – 3 | 80 | 40 | 80 | 50 | 100 | 60 |
| 3 – 4 | 60 | 0 | 80 | 0 | 30 | 0 |
| 4 – 5 | 30 | 0 | 40 | 0 | 10 | 0 |
| 5 – 6 | 10 | 0 | 10 | 0 | 0 | 0 |
| 6 – 7 | 0 | 0 | 0 | 0 | 0 | 0 |
| 7 – 8 | 0 | 0 | 0 | 0 | 0 | 0 |
| 9 – 10 | 0 | 0 | 0 | 0 | 0 | 0 |

Note
[A] means urethane emulsion [A].

Table 3

| Herbicide | Amount of herbicide (Kg) | Urethane emulsion [A] | Herbicidal effect Digitaria adscendens | Amaranthus retroflexus |
|---|---|---|---|---|
| D B N | 0.1 | added | 4.5 | 5 |
| D B N | 0.1 | — | 2 | 3 |
| C-IPC | 0.1 | added | 5 | 4 |
| C-IPC | 0.1 | — | 2 | 0 |
| E P T C | 0.2 | added | 4 | 3.5 |
| E P T C | 0.2 | — | 0 | 0 |
| Trifluralin | 0.05 | added | 5 | 4.5 |
| Trifluralin | 0.05 | — | 3 | 2 |
| Untreated | | | 0 | 0 |

EXAMPLE 2

28 parts of polyethylene glycols (MW 2,000), 50 parts of polyester diol (MW 1,000) prepared from butanediol and adipic acid and 22 parts of TDI were reacted as in Example 1 with the exception that the reaction temperature was 80°–90° C. The urethane prepolymer having 5.2% of isocyanate radicals was obtained. To 100 parts of this prepolymer there were added 3 parts of polyoxyethylene nonylphenyl ether and 12 parts of alkylethersulfate at 20° C., and then the mixture was emulsified in 170 parts of water with continuous agitating to obtain urethane emulsion [B]. The film from the emulsion [B] had WVP of 1,052 g/m²/24 hrs and the soil fixity of 84%. Using 5 Kg of urethane emulsion [B], the herbicidal effect and the degree of phytotoxicity to radish and wheat were observed by the same method as described in Example 1. The resulting data are presented in Table 4.

Table 4

| Herbicide | Amount of herbicide (Kg) | Urethane emulsion [B] | Herbicidal effect | | Phytotoxicity | |
|---|---|---|---|---|---|---|
| | | | Digitaria adscendens | Amaranthus retroflexus | Wheat | Radish |
| Atrazine | 0.05 | added | 5 | 5 | 0 | 0 |
| Atrazine | 0.05 | — | 4 | 4 | 2 | 3 |
| Bromacil | 0.05 | added | 5 | 5 | 0 | 1 |
| Bromacil | 0.05 | — | 5 | 5 | 2 | 5 |
| Diphenamid | 0.1 | added | 5 | 4 | 0 | 0 |
| Diphenamid | 0.1 | — | 3 | 3 | 2 | 0 |
| D P A | 0.3 | added | 4 | 0 | 0 | 0 |
| D P A | 0.3 | — | 2.5 | 0 | 2.5 | 0 |
| Picloram | 0.05 | added | 5 | 5 | 0 | 0 |
| Picloram | 0.05 | — | 2 | 5 | 0 | 2 |
| C-IPC | 0.1 | added | 5 | 5 | 0 | 0 |
| C-IPC | 0.1 | — | 3 | 2 | 0 | 0 |
| E P T C | 0.2 | added | 5 | 5 | 1 | 0 |
| E P T C | 0.2 | — | 4 | 2.5 | 5 | 0 |
| Trifluralin | 0.05 | added | 5 | 5 | 0 | 0 |
| | 0.05 | — | 3.5 | 4 | 2.5 | 0 |
| Urethane emulsion [B] only | | | 0 | 0 | 0 | 0 |

The results in Table 4 show that the similar excellent effects to Example 1 are also obtained in Example 2. These excellent results are also supported by the data in Table 5 and 6.

Table 5

| Depth of the soil | Phytotoxicity to radish | | Phytotoxicity to radish | | Phytotoxicity to sawa millet | |
|---|---|---|---|---|---|---|
| | Atrazine only | Atrazine and [B] | Picloram only | Picloram and [B] | Bromacil only | Bromacil and [B] |
| 0 – 1$_{cm}$ | 70 (%) | 100 (%) | 50 (%0 | 90 (%) | 100 (%) | 100 (%) |
| 1 – 2 | 80 | 100 | 70 | 100 | 100 | 100 |
| 2 – 3 | 80 | 30 | 80 | 50 | 100 | 40 |
| 3 – 4 | 60 | 0 | 80 | 0 | 30 | 0 |
| 4 – 5 | 30 | 0 | 40 | 0 | 10 | 0 |
| 5 – 6 | 10 | 0 | 10 | 0 | 0 | 0 |
| 6 – 7 | 0 | 0 | 0 | 0 | 0 | 0 |
| 7 – 8 | 0 | 0 | 0 | 0 | 0 | 0 |
| 8 – 9 | 0 | 0 | 0 | 0 | 0 | 0 |
| 9 – 10 | 0 | 0 | 0 | 0 | 0 | 0 |

Note 1
[A] means urethane emulsion [B].
Note 2
Test method is the same as in Table 2 (Example 1).

Table 6

| Herbicide | Amount of herbicide (Kg) | Urethane emulsion [B] | Herbicidal effect | |
|---|---|---|---|---|
| | | | Digitaria adscendens | Amaranthus retroflexus |
| C-IPC | 0.1 | added | 5 | 4 |
| C-IPC | 0.1 | — | 2 | 0 |
| E P T C | 0.2 | added | 4 | 3.5 |
| E P T C | 0.2 | — | 0 | 0 |
| Trifluralin | 0.05 | added | 5 | 5 |
| Trifluralin | 0.05 | — | 3 | 2 |

Note
Test method is the same as in Table 3.

EXAMPLE 3

10 parts of mixture [I] (30 parts of methylmethacrylate, 25 parts of butylacrylate, 25 parts of hydroxyethylmethacrylate, 20 parts of acrylic acid), 30 parts of mixture [II] (3 parts of polyoxyethylene nonylphenyl ether, 5 parts of sodium laurylsulfosuccinate, 0.2 part of sodium bisulfite, 150 parts of water), and 4 parts of 2.5 weight % solution of potassium persulfate were charged to the reaction vessel equipped with an agitator and polymerized at 55° C. for 1 hr., after substitution of the air with nitrogen gas. Additionally, 90 parts of the mixture [I], 120 parts of the mixture [II] and 16 parts of 2.5 weight % solution of potassium persulfate were added dropwise separately over 4 hrs., followed by aging for 3 hrs. to obtain the acrylic emulsion [C]. The film from this emulsion [C] had WVP of 495 g/m$^2$/24 hrs and a soil fixity of 52%.

Using 5.0Kg of the emulsion [C], the herbicidal effect and the degree of phytotoxicity to radish and wheat were observed in the same method as described in Example 1. The resulting data are presented in Table 7.

Table 7

| Herbicide | Amount of herbicide (Kg) | Acrylic emulsion [C] | Herbicidal effect | | Phytotoxicity | |
|---|---|---|---|---|---|---|
| | | | Digitaria adscendens | Amaranthus retroflexus | Wheat | Radish |
| Atrazine | 0.05 | added | 5 | 5 | 0 | 0 |
| Atrazine | 0.05 | — | 4 | 4 | 2 | 3 |
| Bromacil | 0.05 | added | 5 | 5 | 0 | 0 |
| Bromacil | 0.05 | — | 5 | 5 | 2 | 5 |
| Diphenamid | 0.1 | added | 4 | 4 | 0 | 0 |
| Diphenamid | 0.1 | — | 3 | 3 | 2 | 0 |
| D P A | 0.3 | added | 4 | 0 | 0 | 0 |

Table 7-continued

| Herbicide | Amount of herbicide (Kg) | Acrylic emulsion [C] | Herbicidal effect Digitaria adscendens | Amaranthus retroflexus | Phytotoxicity Wheat | Radish |
|---|---|---|---|---|---|---|
| D P A | 0.3 | — | 2.5 | 0 | 2.5 | 0 |
| Picloram | 0.05 | added | 4 | 5 | 0 | 0 |
| Picloram | 0.05 | — | 2 | 5 | 0 | 2 |
| C-IPC | 0.1 | added | 4.5 | 4 | 0 | 0 |
| C-IPC | 0.1 | — | 3 | 2 | 0 | 0 |
| E P T C | 0.2 | added | 5 | 4 | 1 | 0 |
| E P T C | 0.2 | — | 4 | 2.5 | 5 | 0 |
| Trifluralin | 0.05 | added | 5 | 5 | 0 | 0 |
| Trifluralin | 0.05 | — | 3.5 | 4 | 2.5 | 0 |
| Acrylic | emulsion [C] only | | 0 | 0 | 0 | 0 |

EXAMPLE 4

47 parts of dimethylterephthalate, 53 parts of polyethylene glycol (MW 200), 0.2 part of ferrous benzoate, 0.1 part of sodium phosphite were charged into the reaction vessel equipped with an agitator, thermometer, nitrogen bubbling tube and high vacuum evaporator. The mixture was reacted at 180° C. for 3 hrs. and then at 270° C. below 1 mm Hg for 16 hrs. Condensed methanol escaped during the reaction. 100 parts of the obtained polyester resin were dissolved in 60 parts of dimethylformamide and then 10 parts of ethyleneoxide adducts of hydrogenated castor oil and 5 parts of sodium alkylbenzenesulfonate were added. Above mixture was emulsified into 205 parts of water to obtain polyester emulsion [D]. The film from this emulsion [D] had WVP of 674 g/m$^2$/24 hrs. and soil fixity of 70%.

Using 6.7 Kg. of the emulsion [D], the herbicidal effect and the degree of phytotoxicity to radish and wheat were observed in the same method as described in Example 1. The resulting data are presented in Table 8.

Table 8

| Herbicide | Amount of Herbicide (Kg) | Polyester emulsion [D] | Herbicidal effect Digitaria adscendens | Amaranthus retroflexus | Phytotoxicity Wheat | Radish |
|---|---|---|---|---|---|---|
| Atrazine | 0.05 | added | 5 | 5 | 0 | 0 |
| Atrazine | 0.05 | — | 4 | 4 | 2 | 3 |
| Bromacil | 0.05 | added | 5 | 5 | 0 | 0 |
| Bromacil | 0.05 | — | 5 | 5 | 2 | 3 |
| Diphenamid | 0.1 | added | 4.5 | 4 | 0 | 0 |
| Diphenamid | 0.1 | — | 3 | 3 | 2 | 0 |
| D P A | 0.3 | added | 4 | 0 | 0 | 0 |
| D P A | 0.3 | — | 2.5 | 0 | 2.5 | 0 |
| Picloram | 0.05 | added | 4.5 | 5 | 0 | 0 |
| Picloram | 0.05 | — | 2 | 5 | 0 | 2 |
| C-IPC | 0.1 | added | 5 | 4.5 | 0 | 0 |
| C-IPC | 0.1 | — | 3 | 2 | 0 | 0 |
| E P T C | 0.2 | added | 5 | 4.5 | 1 | 0 |
| E P T C | 0.2 | — | 4 | 2.5 | 5 | 0 |
| Trifluralin | 0.05 | added | 5 | 5 | 0 | 0 |
| Trifluralin | 0.05 | — | 3.5 | 4 | 2.5 | 0 |
| Polyester | emulsion [D] only | | 0 | 0 | 0 | 0 |

EXAMPLE 5

100 parts of urethane emulsion [A] obtained in Example 1, 30 parts of Bromacil and 230 parts of bentonite were kneaded for about 15 minutes. The obtained massive mixture was formed by pelletizer and dried to obtain small pellets (1-2 mm long, 0.8 mm in diameter) containing 10 wt % of Bromacil.

EXAMPLE 6

Five of experimental plots were arranged in the testing farm. To experimental plot 1-4 (Ex. —1 ~ 4) the spraying samples, which were prepared according to the following table, were sprayed in amount of 200 ml/m$^2$.

Table 9

| Experimental plots | Liquid sample Herbicide | Resins | Water |
|---|---|---|---|
| Ex-1 | Hybar-X 0.8 Kg | Urethane emulsion [A] 10 Kg | 200 l |
| Ex-2 | Hybar-X 0.8 Kg | Urethane emulsion [B] 10 Kg | 200 l |
| Ex-3 | Hybar-X 0.8 Kg | Acrylic emulsion [C] 10 Kg | 200 l |
| Ex-4 | Hybar-X 0.8 Kg | Polyester emulsion [D] 13 Kg | 200 l |

Note
Hybar-X is the herbicide containing Uracil as active ingredient (80%).

To experimental plot 5 (Ex. —5) the Bromacil pellets, which were prepared in Example 5, were applied at amount of 6.4 g/m$^2$. Then, dried weight of weeds per 1 m$^2$ in 5 plots were determined periodically. The resulting data are showed in Table 10 along with the data, for comparison, in check plot 1-6 (Ck- 1 ~ 6). Ck-1 was the untreated plot, Ck-2 was treated with 0.8 g/m$^2$ of Hybar-X solution in water 200 ml. Ck-3 was treated with the mixture spray of Hybar-X 0.8 g, the conventional polyacrylic emulsion 8 g (concentration 50 wt %) and water 200 ml per m$^2$, Ck-4 was treated with the mixture spray of Hybar-X 0.8 g, polyvinylacetate-ethylene copolymer emulsion (concentration 50 wt %) 8 g and water 200 ml per m$^2$, Ck-5 was treated with the mixture spray of Hybar-X 0.8 g, reaction product [of 80 parts of poly(oxyethylene oxypropylene) glycol (MW 4,000, EO/PO=80/20 molar ratio) and 20 parts of tolylenediisocyanate] 8 g, and water 160 ml per m$^2$, and Ck-6 was treated with the mixture spray of Hybar-X 0.8 g, water-soluble polyacrylate (acrylamide/acrylic acid = 80/20 weight ratio; concentration 25 wt %) 16 g, and water 200 ml per m².

Weeds used in this testing farm were in the weight ratio of Gramineous weed/Compositous weed/Broad-leaved weed/othes = 25/40/20/15.

This test started at the middle of February.

Table 10

| Plots | Permeability of resin (g/m²/24hrs) | Soil fixity (%) | Dried weight before spray (g/m²) | Dried weight 3 months after sprayed (g/m²) | Dried weight 6 months after sprayed (g/m²) | Dried weight 10 months after sprayed (g/m²) |
|---|---|---|---|---|---|---|
| Ex-1 | 807 | 78 | 73 | 0 | 116 | 107 |
| Ex-2 | 1,052 | 84 | 62 | 0 | 98 | 92 |
| Ex-3 | 495 | 52 | 57 | 28 | 212 | 245 |
| Ex-4 | 674 | 70 | 66 | 14 | 147 | 163 |
| Ex-5 | 807 | 78 | 45 | 47 | 155 | 171 |
| Ck-1 | — | — | 50 | 508 | 2,025 | 2,172 |
| Ck-2 | — | — | 47 | 86 | 1,088 | 1,269 |
| Ck-3 | 125 | 21 | 59 | 205 | 1,182 | 1,317 |
| Ck-4 | 369 | 46 | 64 | 107 | 856 | 878 |
| Ck-5 | 1,807 | 96 | 77 | 53 | 818 | 844 |
| Ck-6 | at least 3,000 | 34 | 56 | 95 | 1,103 | 1,347 |

Note
The dried weight (g/m²) means the weight of weeds in 1 m² plots after drying at 80° C. for 24 hrs.

The results in Table 10 show that the composition of this invention gives the excellent result in the point of long range effectiveness in comparison with Check plots 1 - 6.

FIG. 1 illustrates the above result in graph, in which X - axis indicates the WVP of used resins, Y - axis indicates the ratio of dried weight of weeds after 10 months to dried weight of weeds before spray.

EXAMPLE 7

The continuous effect of the emulsion [A] obtained in Example 1 was observed by using the mixture of 10 ml of DDVP emulsion (Dimethyl-2,2-dichlorovinyl-phosphate, insecticide), 200g of the emulsion [A], and 10 l of water. With the resulting mixture there was treated a tomato seedling and the occurrence of plant-louse 30 days after sprayed was observed. The resulting data was showed in Table 11. Additionally, comparative example 1 was the result of the untreated plot, comparative example 2 was the result of the check plot which was treated with a single application of a mixture of DDVP emulsion 10 ml and 10 l water, comparative example 3 was the result of the check plot which was treated with three times applications of a mixture of DDVP emulsion 10 ml and 10 l water at the interval of 7 days, and comparative example 4 was the result of the check plot which was treated with the mixture spray of polyvinyl acetate-ethylene copolymer emulsion (mentioned in Example 6) 160g, DDVP emulsion 10 ml and water 10 l.

Table 11

| Spray | Occurrence % |
|---|---|
| Example 7 | 8.2 |
| Comparative example 1 | 100 |
| Comparative example 2 | 73.5 |
| Comparative example 3 | 7.8 |
| Comparative example 4 | 84.0 |

Note
Occurrence was determined on the base of occurrence (100%) in the untreated plot.

What is claimed is:

1. An agricultural chemical composition of improved efficiency, long range effectiveness and decreased phtotoxicity to desirable plants, which comprises: a herbicidally effective amount of a herbicide and a film-forming polyurethane resin emulsion or organic solvent solution containing hydrophilic groups and having a soil fixity of at least 40% and a water vapor permeability of 400-1500 g/m²/24 hrs.

2. The agricultural chemical composition of claim 1, wherein said polymer is in the form of an emulsion.

3. The agricultural chemical composition of claim 1, wherein said polyurethane resin is a reaction product of a polyol having a polyoxyethylene chain with a molecular weight of 300–10,000 in the molecule and a polyisocyanate.

4. The agricultural chemical composition of claim 1, wherein the weight ratio of said herbicide to said polyurethane resin is 1:0.1–200.

5. A method of improving efficiency, long range effectiveness, and selectivity of herbicidal compositions, which comprises: applying a herbicidally effective amount of a herbicide and a film-forming polyurethane resin emulsion or organic solvent solution having a soil fixity of at least 40% and a water vapor permeability of 400–1500 g/m²/24 hrs to soil.

* * * * *